(12) United States Patent
Pu et al.

(10) Patent No.: US 8,350,234 B2
(45) Date of Patent: Jan. 8, 2013

(54) PARTICLE BEAM THERAPY SYSTEM

(75) Inventors: Yuehu Pu, Tokyo (JP); Toshihiro Otani, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 0 days.

(21) Appl. No.: 13/127,112

(22) PCT Filed: Dec. 24, 2008

(86) PCT No.: PCT/JP2008/073407
§ 371 (c)(1),
(2), (4) Date: May 2, 2011

(87) PCT Pub. No.: WO2010/073318
PCT Pub. Date: Jul. 1, 2010

(65) Prior Publication Data
US 2011/0204262 A1      Aug. 25, 2011

(51) Int. Cl.
*A61N 5/10*      (2006.01)
(52) U.S. Cl. .............. 250/491.1; 250/492.1; 250/492.3; 378/147; 378/150; 378/152; 378/170; 378/206
(58) Field of Classification Search .............. 250/491.1, 250/492.1, 492.21, 492.22, 492.23, 492.3, 250/503.1, 505.1, 526; 378/145, 147, 150–152, 378/170, 176, 177, 205, 206, 210
See application file for complete search history.

(56) References Cited

U.S. PATENT DOCUMENTS

| 5,039,867 | A | * | 8/1991 | Nishihara et al. | .......... | 250/492.3 |
| 5,684,854 | A | * | 11/1997 | Hughes | .......... | 378/206 |
| 7,247,873 | B2 | | 7/2007 | Arakawa | | |
| 7,579,608 | B2 | | 8/2009 | Takahashi et al. | | |
| 2008/0298553 | A1 | | 12/2008 | Takahashi et al. | | |

FOREIGN PATENT DOCUMENTS

| DE | 3900884 A1 | 7/1990 |
| DE | 69734751 T2 | 8/2006 |
| DE | 102008004445 A1 | 12/2008 |
| JP | 62-186753 U | 11/1987 |
| JP | 6-246015 A | 9/1994 |
| JP | 6-96048 B2 | 11/1994 |
| JP | 10-76019 A | 3/1998 |
| JP | 2008-22896 A | 2/2008 |

OTHER PUBLICATIONS

International Search Report (PCT/ISA/210) issued on Mar. 10, 2009, by Japanese Patent Office as the International Searching Authority for International Application No. PCT/JP2008/073407.
Written Opinion (PCT/ISA/237) issued by Japanese Patent Office as the International Searching Authority for International Application No. PCT/JP2008/073407.
Office Action issued Aug. 10, 2012 in a corresponding German application with an English-language translation, 10 pps.

* cited by examiner

*Primary Examiner* — Bernard E Souw
(74) *Attorney, Agent, or Firm* — Buchanan Ingersoll & Rooney PC (57) ABSTRACT

Light from a light source is made to be reflected by a light source mirror and to pass through a variable collimator, an irradiation field shape shaped by the variable collimator is projected on a photographing screen by the light passed through the variable collimator, a projection portion of the photographing screen is photographed by a photographic device, and an image photographed by the photographic device is analyzed by an image processor.

19 Claims, 7 Drawing Sheets

PARTICLE BEAM THERAPY SYSTEM

TECHNICAL FIELD

The present invention relates to a particle beam therapy system which is intended for the treatment of cancer, malignant tumor or the like and irradiates to treat a patient's diseased part with a particle beam of carbon, proton or the like.

BACKGROUND ART

For the treatment of patient's cancer, malignant tumor or the like, an irradiation region of a particle beam is required to be conformed to the shape of a patient's diseased part in order to irradiate to treat the diseased part with a proper dose of the particle beam. To that end, it is important that the shape of a variable collimator composed of a plurality of leaves is properly set, and in addition, that the distribution of both an irradiation dose in a transverse direction and an irradiation dose in a depth direction is homogenized so as to irradiate the whole diseased part with a homogeneous dose. More particularly, it becomes important to confirm the shape of the variable collimator in order to make the irradiation region of the particle beam conform to the shape of the patient's diseased part during the irradiation procedure.

Incidentally, for example, in the following Patent Document 1 (Japanese Unexamined Patent Publication No. 10-76019), a light source to be actuated during the time when a ray beam is stopped in a step for setting a ray system and an optical element (mirror) extended in a radiation path of the ray beam until outside the range of its irradiation region are provided. Visible light is emitted to the optical element by actuating the light source. The visible light received by the optical element is reflected to pass through a collimator and is irradiated to a patient's body surface; and positioning is performed so that its light irradiation field conforms to a region of a target zone.

Furthermore, in the following Patent Document 2 (Japanese Unexamined Utility Model Publication No. 62-186753), a light source consisting of a lamp, a mirror extended in a radiation path of a ray beam until outside the range of its irradiation region, and a TV camera located near the light source are provided for a simulation using a light irradiation field. Light is emitted to the mirror by actuating the light source. The light received by the mirror is reflected to pass through a variable (movable) collimator and is irradiated to a patient's body surface. The relationship between the light irradiation field and the patient is observed by using the TV camera.

Besides, in the following Patent Document 3 (Japanese Unexamined Patent Publication No. 6-246015), a light source, a mirror A extended in a radiation path of a ray until outside the range of its irradiation region, a mirror B provided between the light source and the mirror A, and a TV camera located near the mirror B are provided for confirmation of an irradiation range using a light irradiation field. Light is emitted to the mirror A by actuating the light source. The light received by the mirror A is reflected to pass through a variable (movable) collimator and is irradiated to a patient's body surface. The relationship between the light irradiation field and the patient is copied from the mirror A to the mirror B, and a state copied to the mirror B is observed by using the TV camera.

Patent Document 1: Japanese Unexamined Patent Publication No. 10-76019
Patent Document 2: Japanese Unexamined Utility Model Publication No. 62-186753
Patent Document 3: Japanese Unexamined Patent Publication No. 6-246015
Patent Document 4: Japanese Examined Patent Publication No. 6-96048

DISCLOSURE OF THE INVENTION

Problems to be Solved by the Invention

By the way, in conventional devices disclosed in the aforementioned respective Patent Documents 1 to 3, the light emitted from the light source is made to be reflected by the mirror and to pass through the variable (movable) collimator, and the light irradiation field irradiated to the patient's body surface is visually confirmed or is confirmed by using the TV camera; however, the shape of a diseased part of cancer or the like shaped by the variable collimator for each patient is not directly confirmed. Therefore, the patient's body surface is not horizontal and is a body surface having a complicated curved surface; and thus, it becomes difficult to confirm a set shape of the variable collimator with good accuracy. Furthermore, the mirror is required to monitor a wide range region that is the whole light irradiation field irradiated to the patient's body surface, is required to be extended until outside the range of the irradiation region of the ray, and is required to secure installation space in a transverse direction; and the length occupied in an irradiation axis direction of the ray also becomes large, being several tens cm and thus the irradiation device having this mirror section will become large.

Further, the shape of the light field on the body surface is monitored by the camera from the upstream side of the variable collimator as means for confirming the shape of the variable collimator. However, in an image photographed by the camera, an upper portion of the variable collimator is directly photographed. Therefore, the upper surface of the variable collimator is diffusely reflected by the light from the mirror; a planar surface portion, a collimator edge, and end portions of the variable collimator are blur; and thus, it is not easy to analyze the edge portion and to extract a two dimensional shape shaped by collimator leaves. Complicated image recognition software is essential to analyze the edge portion and much labor and time are required for its recognition work. In addition, it becomes substantially difficult to confirm the shape with, for example, an accuracy of not higher than 1 mm required for a particle beam therapy system.

Furthermore, in the particle beam therapy system, the shape of the variable collimator is required to be changed for more than 2 times during one treatment irradiation in a layer-stacking conformal irradiation method or the like that is an advanced three-dimensional irradiation method. In the particle beam therapy system, there are many cases where a device referred to as a patient compensator is inserted between the variable collimator and the patient; and in that case, as described in the aforementioned background art, it is impossible that the shape of the variable collimator is projected on the patient's body surface to monitor its projection image.

An object of the present invention is to provide a particle beam therapy system which can confirm the shape of a variable collimator with good accuracy even during irradiation and reduce in size.

Means for Solving the Problems

According to the present invention, there is provided a particle beam therapy system including: a variable collimator which varies the shape of a particle beam which is to be irradiated to an object to be irradiated in conformity to the shape of a diseased part of the object to be irradiated; a light source which is for photographing an irradiation field shape shaped by the variable collimator; a light source mirror which is arranged on a path or trajectory of the particle beam on the upstream side of the variable collimator, and in which light from the light source is made to be reflected and to pass through the variable collimator; a photographing screen which is arranged on the downstream side of the variable collimator, and on which the irradiation field shape shaped by the variable collimator is projected by the light passed through the variable collimator; a photographic device which photographs a projection portion projected on the photographing screen; and an image processor which analyzes an image photographed by the photographic device.

Advantageous Effect of the Invention

According to a particle beam therapy system of the present invention, light from a light source is made to be reflected by a light source mirror and to pass through a variable collimator, an irradiation field shape shaped by the variable collimator is projected on a photographing screen by the light passed through the variable collimator, a projection portion of the photographing screen is photographed by a photographic device, and an image photographed by the photographic device is analyzed by an image processor; thereby having an effect which can confirm the irradiation field shape shaped by the variable collimator with good accuracy.

Objects, features, aspects, and advantageous effects other than described above of the present invention will become more apparent from the following detailed description of the present invention for referring to the accompanying drawings.

BEST MODE FOR CARRYING OUT THE INVENTION

Embodiment 1

Figure 1:
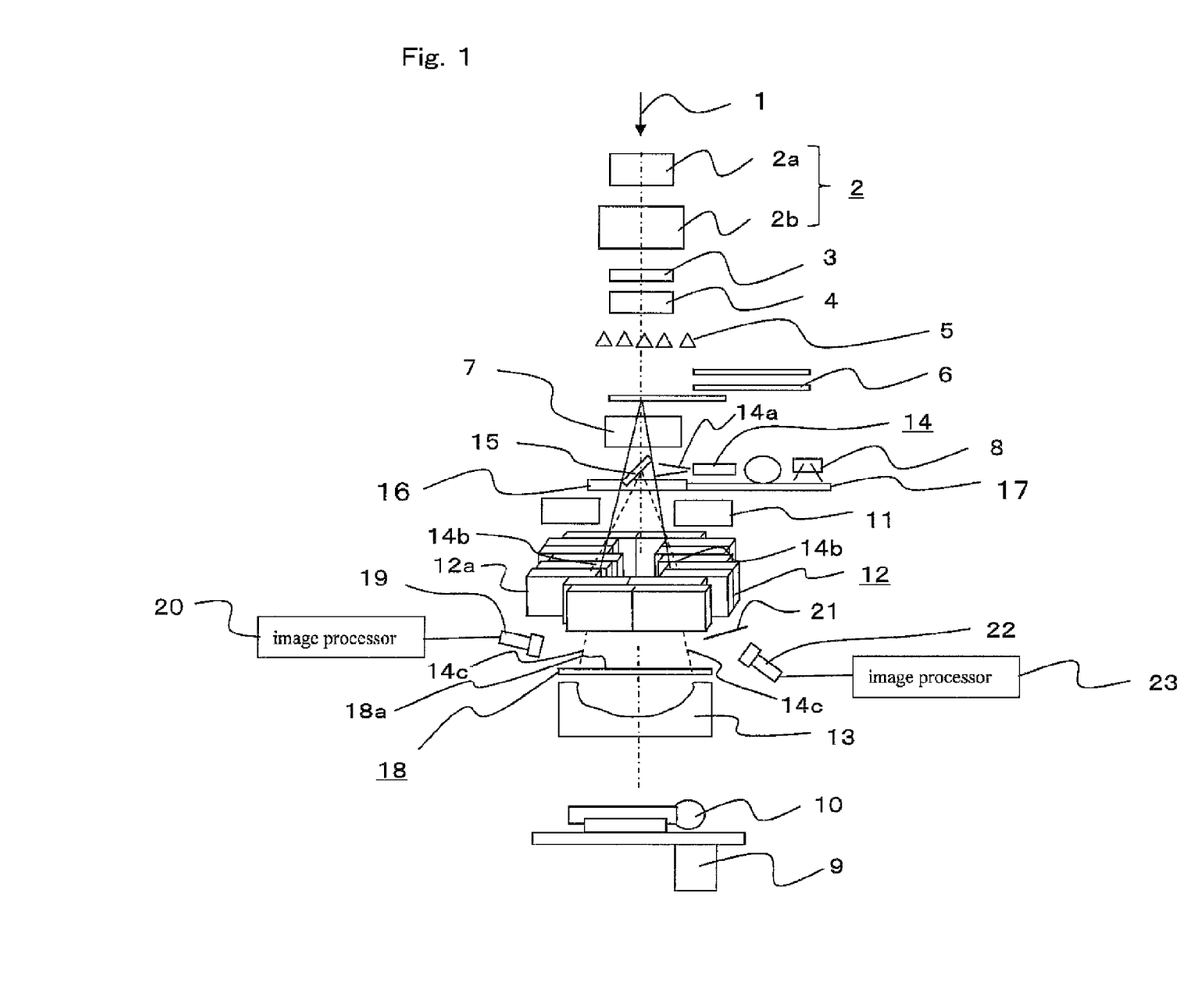
FIG. 1 is a schematic configuration diagram showing a particle beam therapy system according to Embodiment 1 of the present invention.

A particle beam therapy system according to Embodiment 1 of the present invention will be described with reference to a schematic configuration diagram shown in FIG. 1. Incidentally, a variable collimator 12 is shown as a perspective view. In FIG. 1, reference numeral 1 denotes a particle beam of carbon, proton or the like transported from an accelerator (not shown in the drawing), and the particle beam proceeds in an irradiation axis direction. 2 denotes electromagnets which are composed of a pair of electromagnets 2a and 2b and scan a path or trajectory of the particle beam 1 transported from the accelerator. 3 denotes a scatterer which diffuses the particle beam 1 passed through the electromagnets 2; 4 denotes a dose monitor by which an irradiation dose of the particle beam 1 passed through the scatterer 3 is measured; 5 denotes a ridge filter (or energy modulation means) in which an energy spectrum (dose distribution) in a depth direction is adjusted by the thickness of a protruded portion, and in which the particle beam 1 is made to have the energy spectrum corresponding to the depth direction width of a diseased site to be treated; 6 denotes a range shifter which reduces a predetermined amount of energy of the particle beam 1 passed through only set thickness; 7 denotes a flatness monitor which measures the flatness of the particle beam 1 passed through the range shifter 6; and 8 denotes a light localizer which is used for positioning a diseased part of an object to be irradiated 10 that is a patient placed on a treatment bed 9. 11 denotes a fixed collimator which cuts an unnecessary particle beam 1; and 12 denotes the variable collimator which makes the particle beam 1 passed through the fixed collimator 11 shape further and makes the shape of the particle beam conform to the shape of the diseased part of the object to be irradiated 10, and which is configured so that a desired irradiation field shape is formed by varying a plurality of leaves 12a so as to be conformed to the shape of the diseased part of the object to be irradiated 10. 13 denotes a patient compensator (commonly called as a "patient bolus" or "compensation filter") which is used for making the stop position of the particle beam irradiated to the diseased site conform to the diseased site and a normal tissue boundary surface position.

14 denotes a light source which is for photographing the shape of the variable collimator 12; and as an example in the drawing, the light source 14 is provided at a position located on the upstream side from the variable collimator 12. 15 denotes a light source mirror which is arranged on a path or trajectory of the particle beam 1 on the upstream side of the variable collimator 12, and in which light from the light source 14 is made to be reflected and to pass through the variable collimator 12. The light from the light source 14 is emitted from a transverse direction; and therefore, the light source mirror 15 is inclined at approximately 45 degrees to make the light from the light source 14 reflect to the variable collimator 12 side. Incidentally, the light source mirror 15 is made of material through which the particle beam 1 is transmissive. 16 denotes a support body which supports the light source mirror 15; 17 denotes a support base which supports the support body 16; 18 denotes a photographing screen which is arranged on the downstream side of the variable collimator 12, and on which the irradiation field shape of the variable collimator 12 is projected by the light passed through the variable collimator 12; and 18a denotes a projection portion. In addition, the photographing screen 18 is made of material through which the particle beam 1 is transmissive, for example, plastic such as polyethylene, thin sheet or the like. 19 denotes a photographic device which photographs the projection portion 18a projected on the photographing screen 18, and is configured by, for example, a miniature camera. 20 denotes an image processor which analyzes an image photographed by the miniature camera serving as the photographic device 19. 21 denotes a photographing mirror which is for photographing the projection portion 18a projected on the photographing screen 18; and 22 denotes a photographic device which photographs the projection portion 18a of the photographing screen 18 copied on the photographing mirror 21, and is configured by, for example, a miniature camera. 23 denotes an image processor which analyzes an image photographed by the miniature camera serving as the photographic device 22.

The operation of the particle beam therapy system according to the aforementioned Embodiment 1 will be described. A particle beam 1 transported from the accelerator is scanned in a path or trajectory by the electromagnets 2 and passes through the scatterer 3; and accordingly, the particle beam 1 is diffused. The particle beam 1 passed through the scatterer 3 is adjusted in an energy spectrum (dose distribution) in a depth direction by the ridge filter 5. The particle beam 1 passed through the ridge filter 5 is reduced in a predetermined amount of energy of the particle beam 1 by the range shifter 6. The particle beam 1 passed through the range shifter 6 is cut in an unnecessary particle beam 1 by the fixed collimator 11. The particle beam 1 passed through the fixed collimator 11 forms a planned irradiation field shape shaped by the variable collimator 12. The particle beam 1 passed through the variable collimator 12 passes through the patient compensator (bolus) 13 to be shaped corresponding to the shape in a depth direction of a diseased part of an object to be irradiated 10. The particle beam 1 passed through the patient compensator 13 is irradiated to the diseased part of the object to be irradiated 10, and dose distribution corresponding to the three-dimensional shape of a diseased site is formed.

By the way, the light source 14 is made to actuate to emit light 14a in a substantially transverse direction in order to confirm whether the shape of the variable collimator 12 is set as configured. The light 14a is reflected by the light source mirror 15 inclined at approximately 45 degrees to emit light 14b to the variable collimator 12 side and to pass through the variable collimator 12. The shape of the variable collimator 12 is projected on the photographing screen by light 14c passed through the variable collimator 12. The projection portion 18a projected on the photographing screen 18 is photographed by the photographic device 19 consisting of the miniature camera and its image is analyzed by the image processor 20; and accordingly, the shape of the variable collimator 12 can be easily confirmed. Furthermore, as an example in the drawing, the projection portion 18a of the photographing screen 18 copied on the photographing mirror 21 is further photographed by the photographic device 22 consisting of the miniature camera and its image is analyzed by the image processor 23. Incidentally, the aforementioned light source mirror 15, its support body 16, and the photographing screen 18 are formed by material through which the particle beam 1 is easy to pass; and therefore, the particle beam 1 can be reached to the object to be irradiated 10 without a problem.

According to Embodiment 1 of the present invention, the light 14a from the light source 14 is made to be reflected by the light source mirror 15 to emit the light 14b to the variable collimator 12 side, the shape of the variable collimator 12 is projected on the photographing screen 18 by the light 14c passed through the variable collimator 12, the projection portion 18a of the photographing screen 18 is photographed by the photographic devices 19 and 22, and the images photographed by the photographic devices 19 and 22 are analyzed by the image processors 20 and 23; and accordingly, the shape of the diseased part of the object to be irradiated 10 shaped by the variable collimator 12 can be easily confirmed. Furthermore, the shape of the collimator specified by the analysis can be compared with a set image of a collimator shape previously determined based on a treatment plan. In the aforementioned background art, the upper surface of the variable collimator is diffusely reflected by the light from the mirror; therefore, images corresponding to the planar surface portion on the upstream side of the variable collimator and the collimator leaf end portion (portion perpendicular to the aforementioned planar surface portion) are difficult to discriminate, and a leaf edge portion that is a portion in which the aforementioned planar surface portion and the end portion are intersected is a blurred state; and thus, the edge portion is not easy to be extracted by performing image analysis, complicated image recognition software is essential to analyze the edge portion, and much labor and time are required for its recognition work. However, in Embodiment 1 of the present invention, the shape of the diseased part of the object to be irradiated 10 shaped by the variable collimator 12 is projected on the projection portion 18a of the photographing screen 18 by the light 14c passed through the variable collimator 12, and the planar surface portion of the variable collimator 12 and the edge portion in a transverse direction shape of the diseased part shaped on the object to be irradiated 10 that is a patient are extremely clear state by discrimination between positive and negative light or the like; and therefore, there are effects that the complicated image recognition software is not essential to analyze the edge portion, much labor and time are not required for its recognition work, and the analysis can be achieved with good accuracy. In addition, this can also be dealt with confirmation of the shape with, for example, an accuracy of not higher than 1 mm required for the particle beam therapy system.

Furthermore, the color of the photographing screen 18 is usually white; however, the color of the photographing screen 18 consists of a color in which discrimination from the light 14c passed through the variable collimator 12 can be further clearly differentiated or the light emitted from the light source 14 consists of colored light; and accordingly, discrimination between the light 14c passed through the variable collimator 12 and those other than the projection portion 18a of the photographing screen 18 may be further clearly differentiated. In these cases, the edge portion of the variable collimator 12 becomes a clearer state and can be specified with better accuracy.

Furthermore, the mirror of the aforementioned background art is required to copy a wide range region that is the whole light irradiation field irradiated to the patient's body surface and is required to be extended until outside the range of the irradiation region of the ray; and the length occupied in the irradiation axis direction of the ray becomes large, being several tens cm and the irradiation device having this mirror section will become large. However, the light source mirror 15 according to Embodiment 1 of the present invention may only make the light from the light source 14 reflect; and therefore, the light source mirror 15 can be reduced in size in the transverse direction, the length occupied in the irradiation axis direction of the particle beam 1 may be also several cm, for example, 3 to 4 cm, and there is an effect capable of reducing in size of the irradiation section of the particle beam therapy system.

Furthermore, the particle beam 1 is passing through the light source mirror 15 and the photographing screen 18; and therefore, the shape of the variable collimator 12 can be confirmed with good accuracy by the light 14c passed through the variable collimator 12 even during irradiation of the particle beam 1. In addition, in this embodiment, it is desirable to suppress the influence on the particle beam 1 by thinning the thickness of the light source mirror 15, its support body 16, and the photographing screen 18 as much as possible.

Further, even in the case where the shape of the variable collimator 12 is made to change in a treatment step of the object to be irradiated 10 that is the patient, its changed shape can be easily confirmed with good accuracy; and therefore, the irradiation treatment of the particle beam 1 can be continuously performed without giving a stress, a sense of insecurity or the like to the patient. As an example, in the case where so-called three-dimensional layer-stacking irradiation method (see Patent Document 4) which is required to divide the target site for use in the particle beam therapy into a plurality of laminated regions in the depth direction and to irradiate by setting an optimal collimator shape with respect to each layer is carried out, there is an effect that the shape of the set shape of the variable collimator 12 which changes during irradiation can be confirmed with good accuracy.

By the way, as means for photographing the projection portion 18a of the photographing screen 18, the photographic device 19 consisting of the miniature camera and the image processor 20; and the photographing mirror 21, the photographic device 22 consisting of the miniature camera, and the image processor 23 are located; however, a desired purpose can be achieved if either photographing means is selected.

Embodiment 2

Figure 2:
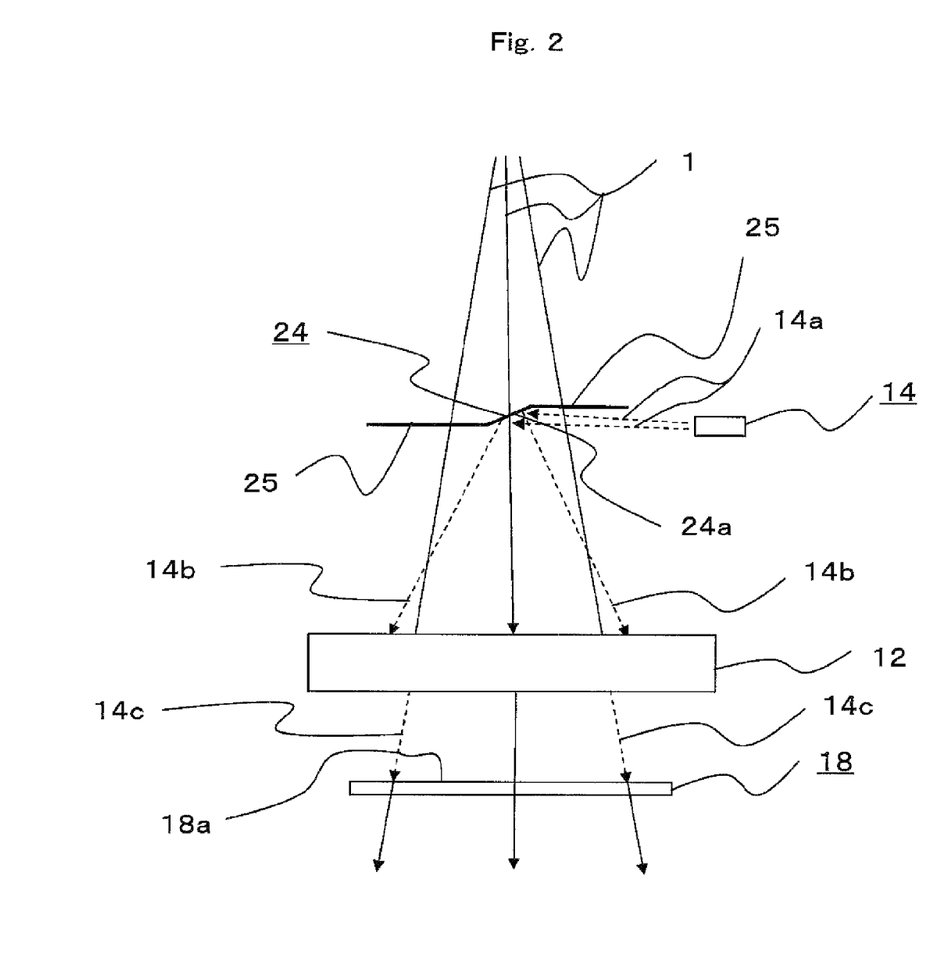
FIG. 2 is a schematic configuration diagram showing a relevant part of a particle beam therapy system according to Embodiment 2 of the present invention.

A relevant part of a particle beam therapy system according to Embodiment 2 of the present invention will be described with reference to a schematic configuration diagram shown in FIG. 2. In FIG. 2, reference numerals 1, 12, 14, 14a, 14b, 14c, 18, and 18a are the same as the configuration of the aforementioned Embodiment 1. 24 denotes a light source mirror which is arranged on a path or trajectory of the particle beam 1 on the upstream side of the variable collimator 12, and in which light from the light source 14 is made to be reflected at a reflecting section 24a and to pass through the variable collimator 12. The light from the light source 14 is emitted from a substantially transverse direction; and therefore, the light source mirror 24 is inclined at approximately 45 degrees to make the light from the light source 14 reflect to the variable collimator 12 side at the reflecting section 24a of the light source mirror 24. Incidentally, the light source mirror 24 is made of material through which the particle beam 1 is transmissive. 25 denotes support bodies which support the light source mirror 24 or one constituent portion of the light source mirror 24.

As is apparent from FIG. 2, in the particle beam therapy system according to Embodiment 2 of the present invention, the light source mirror 24 and the support bodies 25 which support the light source mirror 24 are configured in an integrated structure. As an example in the drawing, the light source mirror 24 is configured such that, for example, a plate made of one sheet of aluminum is bent indifferent levels so that its central portion is inclined at approximately 45 degrees, the central portion is applied with a mirror coating or a mirror-like finishing to form the reflecting section 24a; and portions each connected to one end and the other end of the light source mirror 24 are configured as the support bodies 25. By the way, in order to suppress beam energy loss due to transmission of the particle beam 1 to as low as possible, the plate thickness of aluminum serving as a base material of the light source mirror 24 and the support bodies 25 is preferably approximately 1 mm or not higher than 1 mm, for example, one with a thickness of 0.5 mm or 0.3 mm is used.

According to Embodiment 2 of the present invention, the light source mirror 24 is configured such that the plate made of one sheet of aluminum is bent in different levels so that the central portion is inclined at approximately 45 degrees, and the central portion is applied with a mirror coating (or at least a part of the central portion is applied with a mirror-like finishing or the like so as to form a light reflection surface) to form the reflecting section 24a; and the portions each connected to one end and the other end of the light source mirror 24 are configured as the support bodies 25. Accordingly, the light source mirror 24 can be easily formed, and the support of the light source mirror 24 can be supported by the support bodies 25 configured by the integrated structure; and therefore, a robust support structure can be achieved.

By the way, the description has been made on the case where the material configuring the light source mirror 24 and the support bodies 25 according to Embodiment 2 of the present invention is made of aluminum; however, the material is not limited to this; and aluminum alloy, copper, copper foil, magnesium, plastic, acrylic, polyimide or the like may be permissible; and the same effects are exhibited even the light source mirror 24 is configured such that at least a part of the light source mirror 24 formed by inclining at approximately 45 degrees is applied with a mirror coating, a mirror-like finishing or the like to form the reflecting section 24a. Furthermore, it may be permissible that the light source mirror 24 and its support bodies 25 are made of different material and are integrally configured by combining by means of adhesive or the like so as to have the shape in different levels as shown in FIG. 2; and the same effects are exhibited.

Embodiment 3

As is apparent from FIG. 2, a particle beam therapy system according to Embodiment 3 of the present invention is characterized in that a light source mirror 24 is arranged in an irradiation region of a particle beam 1. Consequently, as described in the mirror of the aforementioned background art, the mirror is not required to be extended until outside the range of the irradiation region of the particle beam 1 and the length occupied in the irradiation axis direction of the particle beam 1 is not also required to be large, being several tens cm, and the light source mirror 24 may only make the light from the light source 14 reflect; and therefore, the light source mirror 24 can be arranged in the irradiation region of the particle beam 1. As a result, the light source mirror 24 can be reduced in size and the length occupied in the irradiation axis direction of the particle beam 1, that is, height can also be reduced. The height of the light source mirror 24 may be several cm, for example, the height can be 3 to 4 cm. As described above, the height in the irradiation direction of the light source mirror 24 can be smaller than the irradiation region of the particle beam 1 in a plane perpendicular to the irradiation direction of the particle beam 1 at the position of the light source mirror 24 and this has an effect that can achieve reduction in size of an irradiation section of the particle beam therapy system.

Embodiment 4

A particle beam therapy system according to Embodiment 4 of the present invention is characterized in that a light source mirror 24 in the aforementioned FIG. 2 is a convex mirror. As described, the light source mirror 24 is the convex mirror and accordingly light from a light source 14 can be further increased in reflection angle by the function of the convex mirror; and therefore, the lengths occupied in a transverse direction and an irradiation axis direction of a particle beam 1 can be further reduced.

Embodiment 5

Figure 3:
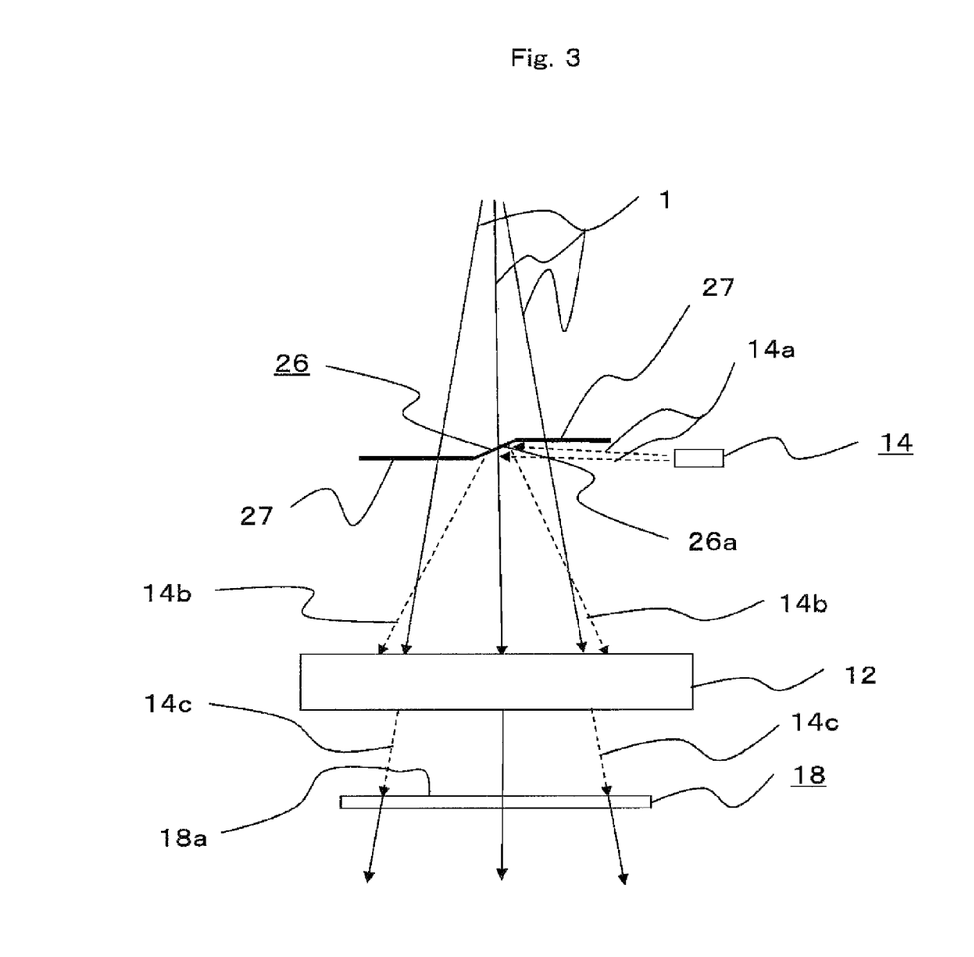
FIG. 3 is a schematic configuration diagram showing a relevant part of a particle beam therapy system according to Embodiment 5 of the present invention.
Figure 4:
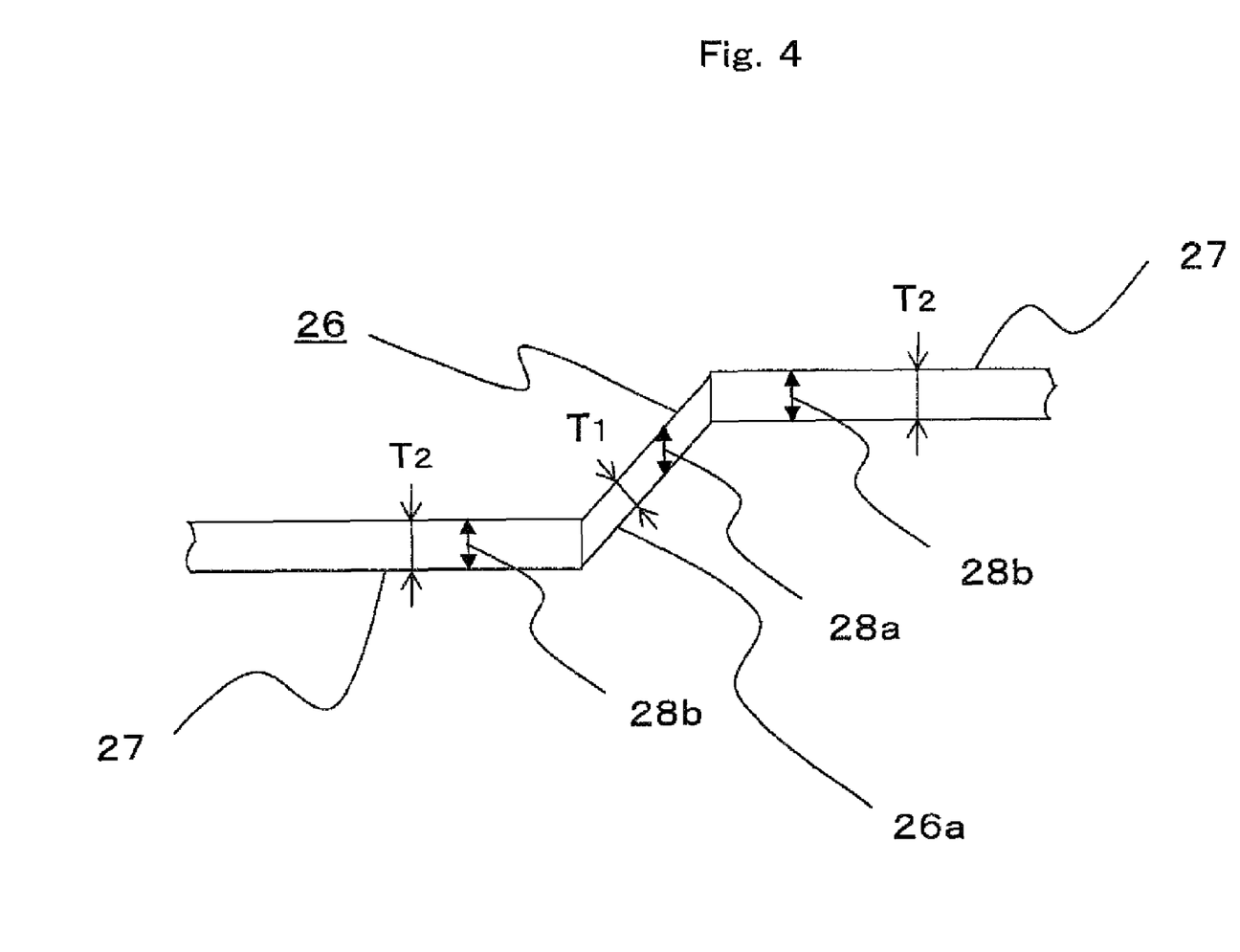
FIG. 4 is an enlarged view showing a light source mirror section of the particle beam therapy system according to Embodiment 5 of the present invention.

A particle beam therapy system according to Embodiment 5 of the present invention will be described with reference to FIG. 3 and FIG. 4. FIG. 3 is a schematic configuration diagram showing a relevant part of a particle beam therapy system and FIG. 4 is an enlarged view showing a light source mirror section of the particle beam therapy system. In these respective drawings, reference numerals 1, 12, 14, 14a, 14b, 14c, 18, and 18a are the same as the configuration of the aforementioned respective Embodiments. 26 denotes alight source mirror which is arranged on a path or trajectory of the particle beam 1 on the upstream side of the variable collimator 12, and in which light from the light source 14 is made to be reflected at a reflecting section 26a and to pass through the variable collimator 12. The light from the light source 14 is emitted from a substantially transverse direction; and therefore, the light source mirror 26 is inclined at approximately 45 degrees to make the light from the light source 14 reflect to the variable collimator 12 side at the reflecting section 26a of the light source mirror 26. Incidentally, the light source mirror 26 is made of material through which the particle beam 1 is transmissive. 27 denotes support bodies which support the light source mirror 26; and in the case where the support bodies 27 are made of the same material as that of the light source mirror 26, the support bodies 27 are configured to be thicker than the plate thickness $T_1$ of the light source mirror 26.

That is, as shown in FIG. 4, it is such that the light source mirror 26 is inclined at approximately 45 degrees (or θ degrees) from the support bodies 27; therefore, the thickness $T_2$ of the support bodies 27 is set to be, for example, 1.414 $T_1$ (or $T_1/\cos(\theta)$); and accordingly, in the particle beam 1, the amount of beam energy loss of a particle beam passing through the light source mirror 26 is configured to be approximately the same value as the amount of beam energy loss of a particle beam passing through the support bodies 27. That is, even the particle beam 1 passes through the light source mirror 26 and the support bodies 27 that are support portions of the light source mirror 26, beam energy of the particle beam 1 reduces by approximately the same value; however, such a configuration can hardly change in the energy distribution of the particle beam 1. This becomes considerably significant for the particle beam therapy system in which the stop position of the particle beam 1 in a patient body is required to be controlled with an accuracy of not higher than approximately 1 mm.

As is apparent from FIG. 3 and FIG. 4, in the particle beam therapy system according to Embodiment 5 of the present invention, the light source mirror 26 and the support bodies 27 which support the light source mirror 26 are configured in an integrated structure. As an example in the drawing, the light source mirror 26 is configured such that, for example, a plate made of one sheet of aluminum is bent in different levels so that its central portion is inclined at substantially 45 degrees, and then, the thickness $T_1$ of the central portion is set to be thinner than the thickness $T_2$ on both sides of the central portion, that is, cutting is performed by grinding or the like so as to be $T_2=1.414$ $T_1$ (or $T_1/\cos(\theta)$), after that, the central portion is applied with a mirror coating or a mirror-like finishing to form the reflecting section 26a; and the portions each connected to one end and the other end of the light source mirror 26 are configured as the support bodies 27.

As described above, the relationship between the plate thickness $T_1$ of the light source mirror 26 and the plate thickness $T_2$ of the support bodies 27 on both sides of the light source mirror 26 is set to be $T_2=1.414$ $T_1$ (or $T_1/\cos(\theta)$); accordingly, in the particle beam 1, the amount of beam energy loss of a particle beam passing through the light source mirror 26 is configured to be approximately the same value as the amount of beam energy loss of a particle beam passing through the support bodies 27, and such a configuration can hardly change in the energy distribution of the particle beam 1; and therefore, the stop position of the particle beam 1 in a patient body can be controlled with an accuracy of not higher than approximately 1 mm, and the particle beam therapy system with stable high reliability can be obtained.

Incidentally, also in Embodiment 5 of the present invention, in order to suppress beam energy loss due to transmission of the particle beam 1 to as low as possible, the plate thickness of a base material of the light source mirror 26 and the support bodies 27 is preferably not higher than approximately several mm, for example, one with a thickness of 0.5 mm or 0.3 mm is used. Furthermore, the light source mirror 26 may only make the light from the light source 14 reflect; and therefore, the light source mirror 26 can be arranged in an irradiation region. As a result, the light source mirror 26 can be reduced in size and the length occupied in an irradiation axis direction of the particle beam 1, that is, height can also be reduced. The height of the light source mirror 26 may be several cm, for example, the height can be 3 to 4 cm. As described above, the height in an irradiation direction of the light source mirror 26 can be smaller than the irradiation region of the particle beam 1 in a plane perpendicular to the irradiation direction of the particle beam 1 at the position of the light source mirror 26 and this has an effect that can achieve reduction in size of an irradiation section of the particle beam therapy system.

Further, the description has been made on the case where the material configuring the light source mirror 26 and the support bodies 27 is made of aluminum; however, the material is not limited to this; and aluminum alloy, copper, copper foil, magnesium, plastic, acrylic, polyimide or the like may be permissible. The light source mirror 26 may be configured such that the central portion formed by inclining at approximately 45 degrees is applied with a mirror coating or a mirror-like finishing to form the reflecting section 26a.

Embodiment 6

Figure 5:
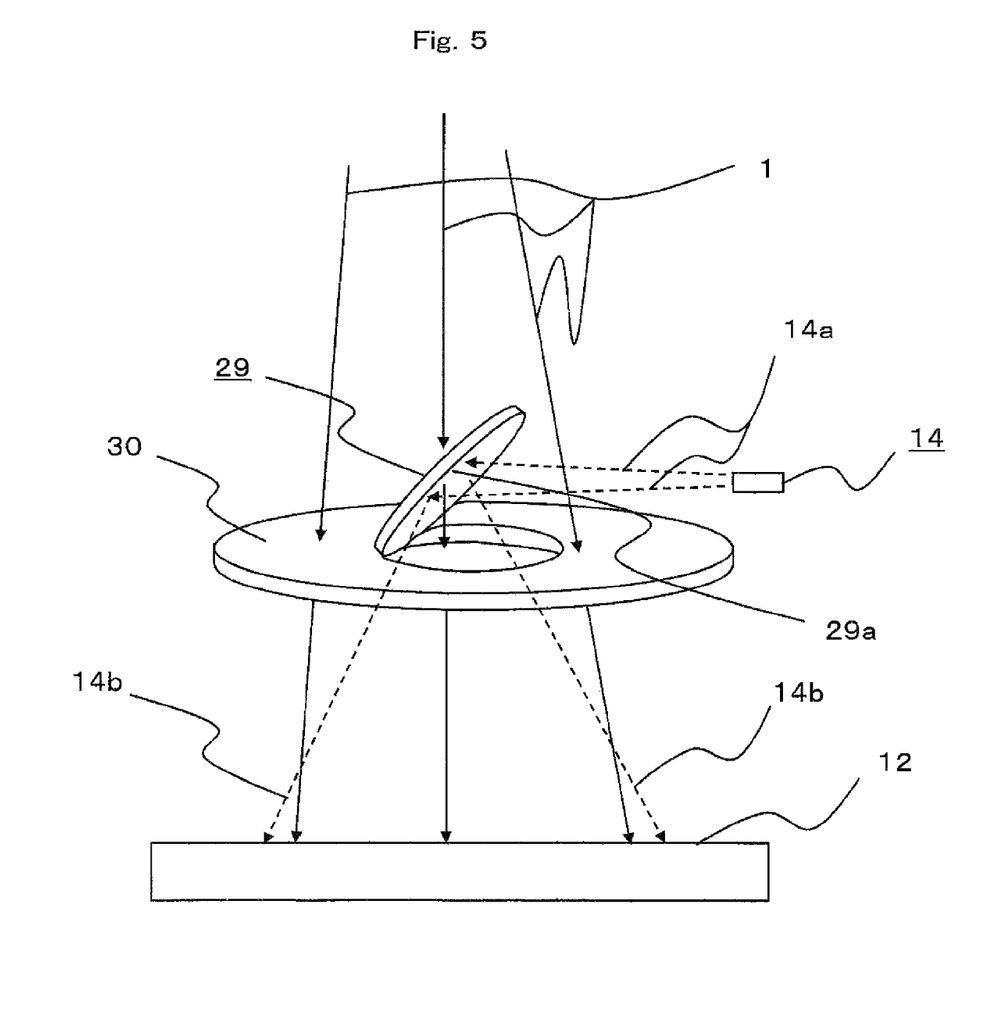
FIG. 5 is a schematic configuration diagram showing a relevant part of a particle beam therapy system according to Embodiment 6 of the present invention.

A particle beam therapy system according to Embodiment 6 of the present invention will be described with reference to FIG. 5. FIG. 5 is a schematic configuration diagram showing a relevant part of the particle beam therapy system. In FIG. 5, reference numerals 1, 12, 14, 14a, and 14b are the same as the configuration of the aforementioned respective Embodiments. 29 denotes a light source mirror which is arranged on a path or trajectory of the particle beam 1 on the upstream side of the variable collimator 12, and in which light from the light source 14 is made to be reflected at a reflecting section 29a and to pass through the variable collimator 12. The light from the light source 14 is emitted from a substantially transverse direction; and therefore, the light source mirror 29 is inclined at approximately 45 degrees to make the light from the light source 14 reflect to the variable collimator 12 side at the reflecting section 29a of the light source mirror 29. Incidentally, the light source mirror 29 is made of material through which the particle beam 1 is transmissive. 30 is a support body which supports the light source mirror 29.

As is apparent from FIG. 5, in the particle beam therapy system according to Embodiment 6 of the present invention, the light source mirror 29 and the support body 30 which supports the light source mirror 29 are configured in an integrated structure. As an example in the drawing, the light source mirror 29 is configured such that, for example, a central portion of a planar circular plate made of one sheet of aluminum is raised up, for example, in a substantially circular shape and is bent so as to be inclined at approximately 45 degrees; and the raised up central portion is applied with a mirror coating to form the reflecting section 29a. By the way, in order to suppress beam energy loss due to transmission of the particle beam 1 to as low as possible, the plate thickness of aluminum serving as a base material of the light source mirror 29 and the support body 30 is preferably not higher than approximately several mm, for example, one with a thickness of 0.5 mm or 0.3 mm is used.

According to Embodiment 6 of the present invention, the light source mirror 29 is configured such that the circular plate made of one sheet of aluminum is raised up and bent so that the central portion is inclined at approximately 45 degrees, the raised up central portion is applied with a mirror coating or a mirror-like finishing to form the reflecting section 29a, and the other portion of the light source mirror 29 is configured as the support body 30. Accordingly, the central portion of the support body 30 may only be raised up and bent, the light source mirror 29 can be easily formed, and the support of the light source mirror 29 can be supported by the support body 30 configured by the integrated structure; and therefore, a robust support structure can be achieved. Furthermore, the light source mirror 29 may only make the light from the light source 14 reflect; and therefore, the light source mirror 29 can be arranged in an irradiation region. As a result, the light source mirror 29 can be reduced in size and the length occupied in an irradiation axis direction of the particle beam 1, that is, height can also be reduced. The height of the light source mirror 29 may be several cm, for example, the height can be 3 to 4 cm. As described above, the height in an irradiation direction of the light source mirror 29 can be smaller than the irradiation region of the particle beam 1 in a plane perpendicular to the irradiation direction of the particle beam 1 at the position of the light source mirror 29 and this has an effect that can achieve reduction in size of an irradiation section of the particle beam therapy system.

By the way, the description has been made on the case where the material configuring the light source mirror 29 and the support body 30 according to Embodiment 6 of the present invention is made of aluminum; however, the material is not limited to this; and aluminum alloy, copper, copper foil, magnesium, plastic, acrylic, polyimide or the like may be permissible; and the same effects are exhibited even the light source mirror 29 is configured such that at least a part of the light source mirror 29 formed by inclining at approximately 45 degrees is applied with a mirror coating, a mirror-like finishing or the like to form the reflecting section 29a.

Incidentally, the description has been made on the case where the shape of the light source mirror 29 is a substantially circular shape; however, the shape is not limited to the circular shape; and even a quadrangular shape and other shape may be permissible. In other words, such shapes may be permissible if the light from the light source 14 is made to be reflected and to pass through the variable collimator 12 and an irradiation field shape shaped by the variable collimator 12 can be projected on a photographing screen 18 by the light passed through the variable collimator 12.

Embodiment 7

A particle beam therapy system according to Embodiment 7 of the present invention is characterized in that a light source mirror 29 in the aforementioned FIG. 5 is a convex mirror. As described, the light source mirror 29 is the convex mirror and accordingly light from a light source 14 can be further increased in reflection angle by the function of the convex mirror; and therefore, the lengths occupied in a horizontal direction and an irradiation axis direction of a particle beam 1 can be further reduced.

Embodiment 8

Figure 6:
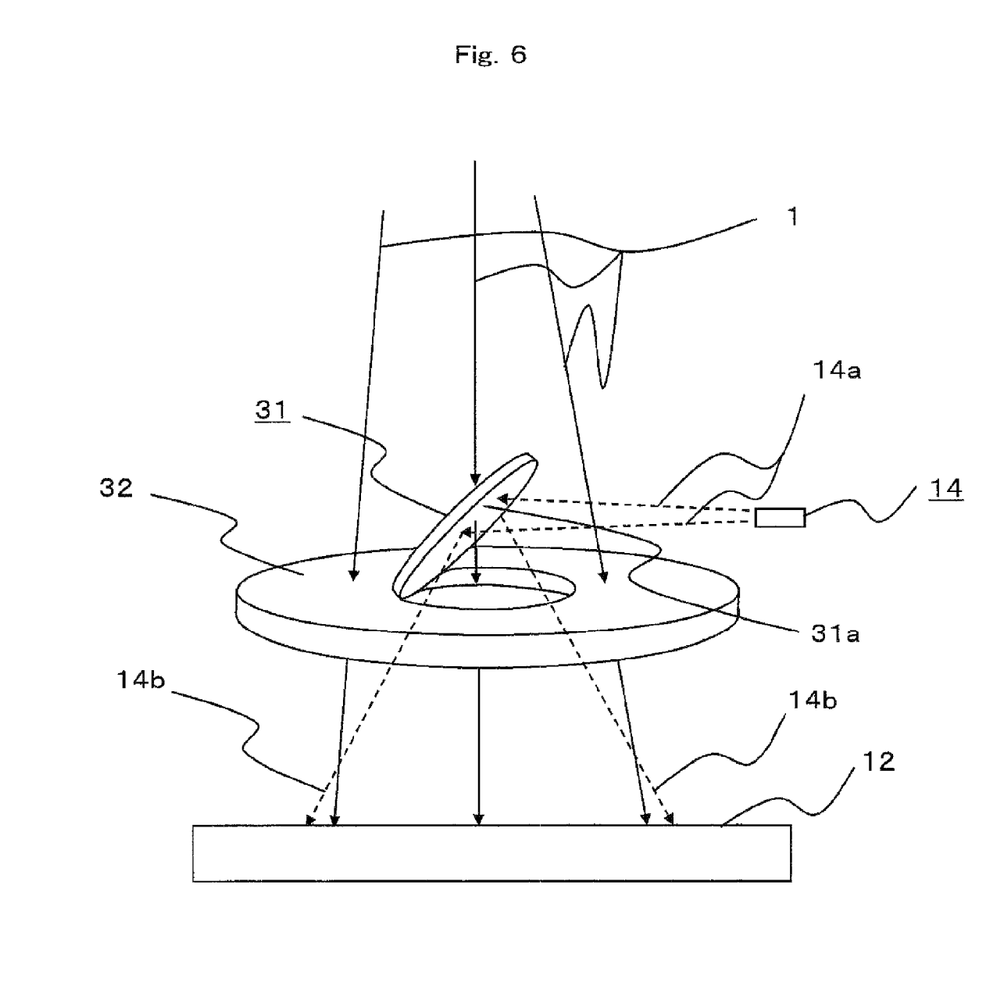
FIG. 6 is a schematic configuration diagram showing a relevant part of a particle beam therapy system according to Embodiment 8 of the present invention.
Figure 7:
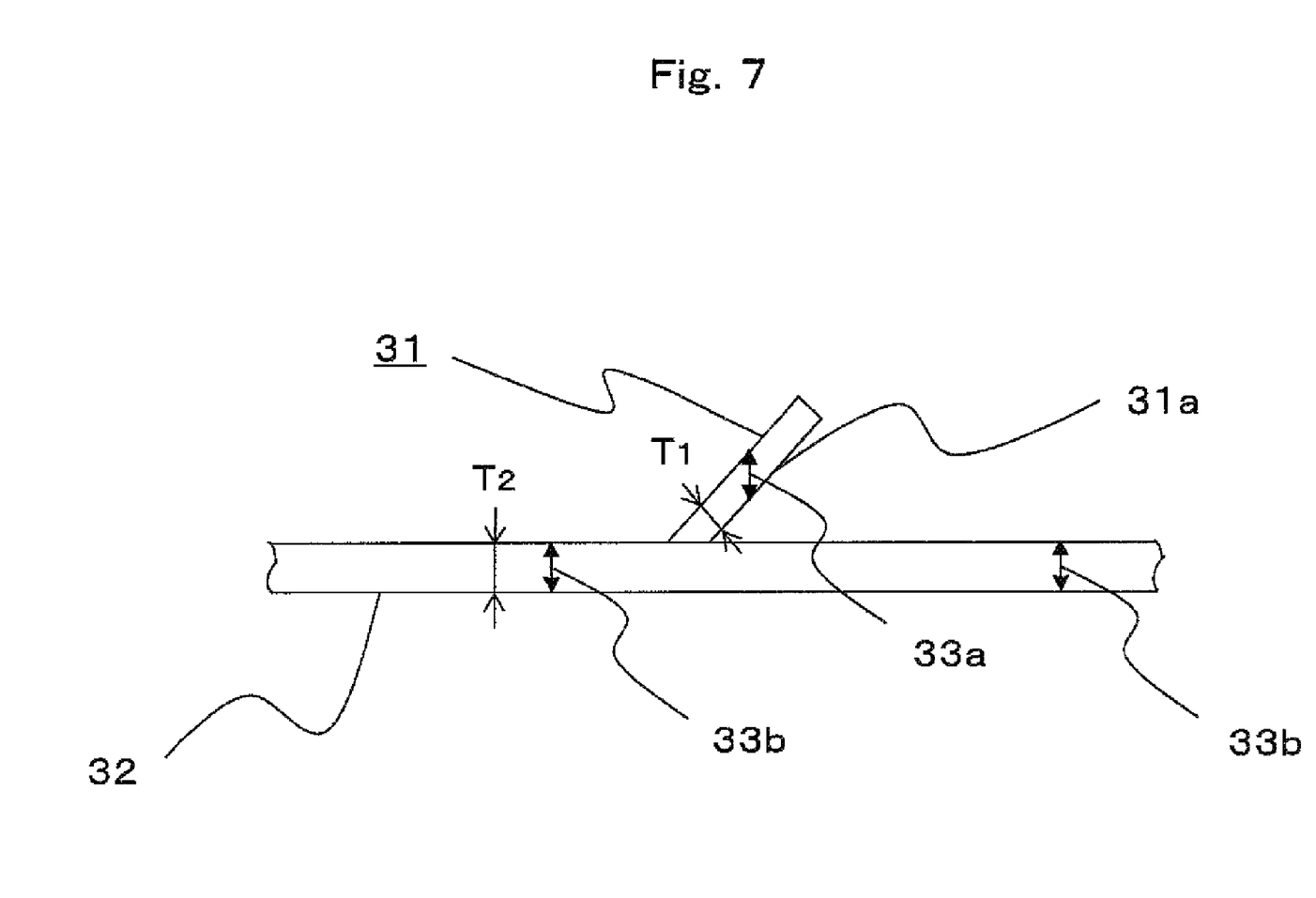
FIG. 7 is an enlarged view showing a light source mirror section of the particle beam therapy system according to Embodiment 8 of the present invention.

A particle beam therapy system according to Embodiment 8 of the present invention will be described with reference to FIG. 6 and FIG. 7. FIG. 6 is a schematic configuration diagram showing a relevant part of a particle beam therapy system and FIG. 7 is an enlarged view showing a light source mirror section of the particle beam therapy system. In these respective drawings, reference numerals 1, 12, 14, 14a, and 14b are the same as the configuration of the aforementioned respective Embodiments. 31 denotes a light source mirror which is arranged on a path or trajectory of the particle beam 1 on the upstream side of the variable collimator 12, and in which light from the light source 14 is made to be reflected at a reflecting section 31a and to pass through the variable collimator 12. The light from the light source 14 is emitted from a substantially transverse direction; and therefore, the light source mirror 31 is inclined at approximately 45 degrees to make the light from the light source 14 reflect to the variable collimator 12 side at the reflecting section 31a of the light source mirror 31. Incidentally, the light source mirror 31 is made of material through which the particle beam 1 is transmissive. 32 is a support body which supports the light source mirror 31 and is configured to be thicker than the plate thickness $T_1$ of the light source mirror 31.

That is, as shown in FIG. 7, the thickness $T_2$ of the support body 32 is set to be, for example, $1.414 T_1$ (or $T_1/\cos(\theta)$); and accordingly, in the particle beam 1, the amount of beam energy loss of a particle beam passing through the light source mirror 31 is configured to be approximately the same value as the amount of beam energy loss of a particle beam passing through the support body 32. That is, even the particle beam 1 passes through the light source mirror 31 and the support body 32 that is a support portion of the light source mirror 31, beam energy of the particle beam 1 reduces by approximately the same value; however, such a configuration can hardly change in the energy distribution of the particle beam 1. This becomes considerably significant for the particle beam therapy system in which the stop position of the particle beam 1 in a patient body is required to be controlled with an accuracy of not higher than approximately 1 mm.

As is apparent from FIG. 6 and FIG. 7, in the particle beam therapy system according to Embodiment 8 of the present invention, the light source mirror 31 and the support body 32 which supports the light source mirror 31 are configured in an integrated structure. As an example in the drawing, the light source mirror 31 is configured such that, for example, a central portion of a planar circular plate made of one sheet of aluminum is raised up, for example, in a substantially circular shape and is bent so as to be inclined at approximately 45 degrees; and the thickness $T_1$ of the raised up central portion is set to be thinner than the thickness $T_2$ on the peripheral side of the central portion, that is, cutting is performed by grinding or the like so as to be $T_2=1.414 T_1$ (or $T_1/\cos(\theta)$), after that, the central portion is applied with a mirror coating or a mirror-like finishing to form the reflecting section 31a; and portions other than the light source mirror 31 are configured as the support body 32.

As described above, the relationship between the plate thickness $T_1$ of the light source mirror 31 and the plate thickness $T_2$ of the support body 32 on the peripheral side of the light source mirror 31 is set to be $T_2=1.414 T_1$ (or $T_1/\cos(\theta)$); accordingly, in the particle beam 1, the amount of beam energy loss of a particle beam passing through the light source mirror 31 is configured to be approximately the same value as the amount of beam energy loss of a particle beam passing through the support body 32, and such a configuration can hardly change in the energy distribution of the particle beam 1; and therefore, the stop position of the particle beam 1 in a patient body can be controlled with an accuracy of not higher than approximately 1 mm, and the particle beam therapy system with stable high reliability can be obtained.

Incidentally, also in Embodiment 8 of the present invention, in order to suppress loss due to transmission of the particle beam 1 to as low as possible, the plate thickness of aluminum serving as a base material of the light source mirror 31 and the support body 32 is preferably not higher than approximately several mm, for example, one with a thickness of 0.5 mm or 0.3 mm is used. Furthermore, the light source mirror 31 may only make the light from the light source 14 reflect; and therefore, the light source mirror 31 can be arranged in an irradiation region. As a result, the light source mirror can be reduced in size and the length occupied in an irradiation axis direction of the particle beam 1, that is, height can also be reduced. The height of the light source mirror 31 may be several cm, for example, the height can be 3 to 4 cm. As described above, the height in an irradiation direction of the light source mirror 31 can be smaller than the irradiation region of the particle beam 1 in a plane perpendicular to the irradiation direction of the particle beam 1 at the position of the light source mirror 31 and this has an effect that can achieve reduction in size of an irradiation section of the particle beam therapy system.

Further, the description has been made on the case where the material configuring the light source mirror 31 and the support body 32 is made of aluminum; however, the material is not limited to this; and aluminum alloy, copper, copper foil, magnesium, plastic, acrylic, polyimide or the like may be permissible; and the same effects are exhibited even the light source mirror 31 is configured such that at least a part of the light source mirror 31 formed by inclining at approximately 45 degrees is applied with a mirror coating, a mirror-like finishing or the like to form the reflecting section 31a. Furthermore, the description has been made on the case where the shape of the light source mirror 31 is a substantially circular shape; however, the shape is not limited to the circular shape; and even a quadrangular shape and other shape may be permissible. In other words, such shapes may be permissible if the light from the light source 14 is made to be reflected and to pass through the variable collimator 12 and an irradiation field shape shaped by the variable collimator 12 can be projected on a photographing screen 18 by the light passed through the variable collimator 12.

Embodiment 9

A particle beam therapy system according to Embodiment 9 of the present invention is characterized in that a light source mirror 31 in the aforementioned FIG. 6 is a convex mirror. As described, the light source mirror 31 is the convex mirror and accordingly light from a light source 14 can be further increased in reflection angle by the function of the convex mirror; and therefore, the lengths occupied in a transverse direction and an irradiation axis direction of a particle beam 1 can be further reduced.

Various modifications and alternations of the invention can be achieved to those skilled in the art without departing from the scope and spirit of this invention, and it should be understood that this is not limited to the illustrative embodiments set forth in the description.

INDUSTRIAL APPLICABILITY

The present invention is suitable to achieve a particle beam therapy system which is intended for the treatment of cancer, malignant tumor or the like and irradiates to treat a patient's diseased part with a particle beam of carbon, proton or the like, the particle beam being irradiated in conformity to the shape of the patient's diseased part.

The invention claimed is:

1. A particle beam therapy system comprising:
a variable collimator which varies the shape of a particle beam which is to be irradiated to an object;
a light source for photographing an irradiation field shape shaped by said variable collimator;
a light source mirror which is arranged on an orbit of the particle beam on the upstream side of said variable collimator, and in which light from said light source is made to be reflected and to pass through said variable collimator;
a photographing screen (i) which is arranged on a downstream side of said variable collimator, (ii) on which the light that passed through said variable collimator is projected, and (iii) through which the particle beam passes;
a photographic device which photographs a projection portion of said photographing screen; and
an image processor which analyzes an image photographed by said photographic device.

2. The particle beam therapy system according to claim 1, wherein said light source mirror is inclined so that the light from said light source is made to be reflected and to pass through said variable collimator, and
further comprising support bodies, each of which is arranged on one end and the other end of said light source mirror and is integrally shaped with said light source mirror, said support bodies being configured in different levels.

3. The particle beam therapy system according to claim 2, wherein said light source mirror is arranged in an irradiation region of the particle beam.

4. The particle beam therapy system according to claim 2, wherein the thickness of said light source mirror is thinner than the thickness of said support bodies, and the amounts of beam energy losses of the particle beams passing through said light source mirror and said support bodies are homogenized to become independent of the position where the particle beams traverse the mirror or supporting bodies.

5. The particle beam therapy system according to claim 1, wherein said light source mirror is configured such that said support body is planar and a central portion of said support body is raised up to form a reflecting section.

6. The particle beam therapy system according to claim 5, wherein the thickness of said light source mirror which is configured by raising up the central portion of said support body is thinner than the thickness of said support body, and the amounts of beam energy loss of the particle beams passing through said light source mirror and said support body are homogenized.

7. The particle beam therapy system according to claim 2, wherein said light source mirror is a convex mirror.

8. The particle beam therapy system according to claim 5, wherein said light source mirror is a convex mirror.

9. The particle beam therapy system according to claim 6, wherein said light source mirror is a convex mirror.

10. The particle beam therapy system according to claim 1, wherein said light source mirror is made of aluminum.

11. The particle beam therapy system according to claim 2, wherein said light source mirror is made of aluminum.

12. The particle beam therapy system according to claim 5, wherein said light source mirror is made of aluminum.

13. The particle beam therapy system according to claim 6, wherein said light source mirror is made of aluminum.

14. The particle beam therapy system according to claim 7, wherein said light source mirror is made of aluminum.

15. The particle beam therapy system according to claim 1, wherein said light source mirror is configured by applying a mirror coating on the surface of plastic.

16. The particle beam therapy system according to claim 2, wherein said light source mirror is configured by applying a mirror coating on the surface of plastic.

17. The particle beam therapy system according to claim 5, wherein said light source mirror is configured by applying a mirror coating on the surface of plastic.

18. The particle beam therapy system according to claim 6, wherein said light source mirror is configured by applying a mirror coating on the surface of plastic.

19. The particle beam therapy system according to claim 7, wherein said light source mirror is configured by applying a mirror coating on the surface of plastic.

* * * * *